United States Patent [19]
Sato et al.

[11] Patent Number: 6,063,409
[45] Date of Patent: May 16, 2000

[54] **SPECIES *CRYPTOCOCCUS NODAENSIS*, A PROCESS FOR PRODUCING SALT-RESISTANT THERMOSTABLE GLUTAMINASE BY USE OF THE SAME, AND A PROCESS FOR PRODUCING GLUTAMIC ACID-RICH PROTEIN HYDROLYSATES**

[75] Inventors: Itsuo Sato; Hiroe Sato; Yoshiki Hanya; Keietsu Abe; Mitsuharu Fujii; Tadanobu Nakadai, all of Chiba, Japan; Jack W. Fell, Key Biscayne, Fla.

[73] Assignee: Kikkoman Corporation, Japan

[21] Appl. No.: 09/211,313

[22] Filed: Dec. 14, 1998

[30] Foreign Application Priority Data

May 28, 1998 [JP] Japan .................................. 10-147630

[51] Int. Cl.⁷ .............................. A23L 1/20; A23J 3/34; C12N 9/80; C12N 1/12
[52] U.S. Cl. ........................ 426/52; 435/228; 435/252.1; 426/46; 426/56; 426/634
[58] Field of Search ................................ 435/228, 252.1; 426/52, 49, 44, 629, 634, 56, 656, 46

[56] References Cited

FOREIGN PATENT DOCUMENTS

| | | |
|---|---|---|
| 59-48759 | 12/1974 | Japan . |
| 94975 | of 1988 | Japan . |
| 1-16465 | 3/1989 | Japan . |
| 6-38748 | 5/1994 | Japan . |

OTHER PUBLICATIONS

Nippon Shoyu Kenkyusho Zasshi 13:18–25 (1987).

Journal of the Brewing Society of Japan 86:441–446 (1991).

Kusunoki et al., "Application of Colorimetric Microdilution Plate Hybridization for Rapid Genetic Identification of 22 Mycobacterium Species," J. Clin. Microbiol. 29:1596–1603 (1991).

*Primary Examiner*—Keith D. Hendricks
*Attorney, Agent, or Firm*—Medlen & Carroll, LLP

[57] ABSTRACT

A microorganism belonging to the genus Cryptococcus having the ability to produce glutaminase excellent in salt resistance and thermostability. Further, this microorganism can be used to produce the salt-resistant thermostable glutaminase, and by use of this glutaminase, glutamic acid-rich and good tasting protein hydrolysates (e.g. flavoring foods such as soy sauce, miso etc.) are produced efficiently in a simple operation. Specifically, said microorganism is the new species *Cryptococcus nodaensis* having assimilability of +, −, − and − toward lactose, N-acetyl-D-glucosamine, D-glucosamine and arbtin as carbon sources, respectively.

8 Claims, 4 Drawing Sheets

SPECIES *CRYPTOCOCCUS NODAENSIS*, A PROCESS FOR PRODUCING SALT-RESISTANT THERMOSTABLE GLUTAMINASE BY USE OF THE SAME, AND A PROCESS FOR PRODUCING GLUTAMIC ACID-RICH PROTEIN HYDROLYSATES

FIELD OF THE INVENTION

The present invention relates to a novel species *Cryptococcus nodaensis*, a process for producing salt-resistant thermostable glutaminase, and a process for producing glutamic acid-rich protein hydrolysates.

BACKGROUND OF THE INVENTION

It is known that glutaminase plays an important role in food industry, particularly in enzymatically degradating protein to produce flavoring foods.

For enzymatically degradating protein, the protein is degradated finally into its constitutional amino acids via peptides by action of various proteolytic enzymes.

Glutamine formed in such cases is readily converted non-enzymatically into tasteless pyroglutamic acid in the absence of glutaminase.

The rate of degradating glutamic acid into pyroglutamic acid is increased with an increasing temperature.

It is known that the coexistence of glutaminase in such a degradation system enables not only prevention of conversion of glutamine into pyroglutamic acid but also conversion of free glutamine into its corresponding amount of glutamic acid.

Enzymatic degradation of protein at high temperatures is a very effective method for raising the rate of degradation of the protein and preventing contamination with microorganisms, thus efficiently producing glutamic acid-rich flavoring foods.

To adopt these conditions, however, it is necessary that usable glutaminase is thermostable.

Further, a method of making soy sauce, miso etc. by fermentation is known as a process for producing glutamic acid-rich flavoring foods by enzymatically degradating protein materials in the presence of high conc. salt. In this case, the presence of high conc. salt is intended to prevent decomposition and putrefaction resulting from microbial contamination.

However, it is known that a lower glutamic acid content after degradation is an inevitable disadvantage in the enzymatic degradation method and this glutamic acid content is considerably lower than in a hydrochloric acid degradation method.

The speculative reason for the lower glutamic acid content in the enzymatic degradation method is that glutaminase is significantly inhibited by high conc. salt in soy sauce flavorings obtained by admixing soy sauce koji with saline, so glutamine released from protein materials by enzyme degradation is rapidly converted into pyroglutamic acid.

For this reason, it is also proposed that separately prepared glutaminase is added to soy sauce flavorings to convert them into glutamic acids. However, because the glutaminase added in this method is not resistant to salt, salt is initially mixed at a concentration as low as about 7 to 8%, and the glutaminase is then allowed to act for a predetermined period of time, followed by supplementing the materials with salt to an usual salt concentration of 15% or more for flavorings.

However, microbial contamination cannot be prevented in the presence of salt at such low concentration, so there is the risk of deterioration in qualities of the product.

The problem with simultaneous use of this kind of glutaminase is that the glutaminase used is not resistant to salt, and that the procedures of initially adding low concentration of salt and then raising the concentration of salt are cumbersome.

Accordingly, it is important to obtain a glutaminase capable of acting adequately even in the presence of high conc. of salt.

*Candida famata* (Japanese Patent Publication No. 38748/1994) and *Cryptococcus albidus* (Japanese Patent Publication No. 48759/1974) are known respectively to produce glutaminases having salt resistance and thermostability.

However, the relative activity of the former in the presence of 18% salt is as low as 50% relative to 100% activity in the absence of salt, so there is the disadvantage of its inability to act adequately in the presence of high conc. salt. Similarly, the activity of the latter in the presence of 18% salt is also as low as 70% and is thus not satisfactory.

The former and latter glutaminases are thermostable up to 60° C. respectively and are not satisfactory as compared with the thermostability of other kind of enzymes, so the advent of glutaminase further superior in thermostability is desired.

Accordingly, the object of the present invention is to obtain a microorganism having the ability to produce glutaminase significantly excellent in salt resistance and thermostability capable of acting adequately even in treatment at high temperatures in the presence of high conc. salt, and to produce salt-resistant thermostable glutaminase by use of this microorganism, as well as to acquire glutamic acid-rich protein hydrolysates (e.g. soy sauce) efficiently in a simple operation.

SUMMARY OF THE INVENTION

As a result of eager study for solving this problem, we found that one strain belonging to the genus Cryptococcus newly separated from the soil, that is, *Cryptococcus nodaensis* G60, produces a salt-resistant thermostable glutaminase as shown in Table 1. Comparison of the salt resistance, thermostability and other characteristics of this enzyme with those of the enzymes produced by known microorganisms gave the results in Table 1. The glutaminase derived from *Cryptococcus nodaensis* G60 possesses significantly excellent salt resistance similar to that of the glutaminase derived from *Bacillus subtilus*, and further possesses significantly high thermostability never known (higher by 5° C. than that of the enzymes derived from *Cryptococcus albidus* and *Candida famata*), and on the basis of this finding, the present invention was completed.

TABLE 1

Comparison in enzymatic characteristics among glutaminases derived from microorganisms

| glutaminase-producing microorganisms | optimum pH | relative activity in the presence of 18% salt | thermo-stability ° C. | optimum temp. ° C. |
|---|---|---|---|---|
| *Cryptococcus nodaensis* | 5.0–8.0 | 85 | 65 | 70 |
| *Cryptococcus albidus* (Note 1) | 5.5–8.5 | 50 | 60 | 70 |

TABLE 1-continued

Comparison in enzymatic characteristics among glutaminases derived from microorganisms

| glutaminase-producing microorganisms | optimum pH | relative activity in the presence of 18% salt | thermo-stability °C. | optimum temp. °C. |
|---|---|---|---|---|
| *Candida famata* (Note 2) | 6.5–8.5 | 70 | 60 | 60 |
| *Bullera alba* (Note 3) | 6.0–9.0 | 80 | — | — |
| *Aspergillus sojae* (Note 1) | 7.5–8.5 | 6 | 45 | — |
| *Aspergillus niger* (Note 4) | 5.0–7.5 | 75 | 55 | 70 |
| *Escherichia coli* (Note 1) | 5.0 | 65 | 45 | — |
| *Bacillus subtilus* (Note 5) | 6.0 | 90 | 45 | — |

Note 1) Nippon Shoyu Kenkyusho Zasshi, vol. 13, No. 1, pp. 18–25 (1987)
Note 2) Japanese Laid-Open Patent Publication No. 94975/1988
Note 3) Japanese Patent Publication No. 16465/1989
Note 4) Lipase A "Amano" (Amano Pharmaceutical Co., Ltd.)
Note 5) Journal of the Brewing Society of Japan, vol. 86, No. 6, pp. 441–446 (1991)

DETAILED DESCRIPTION OF THE INVENTION

Figure 1:
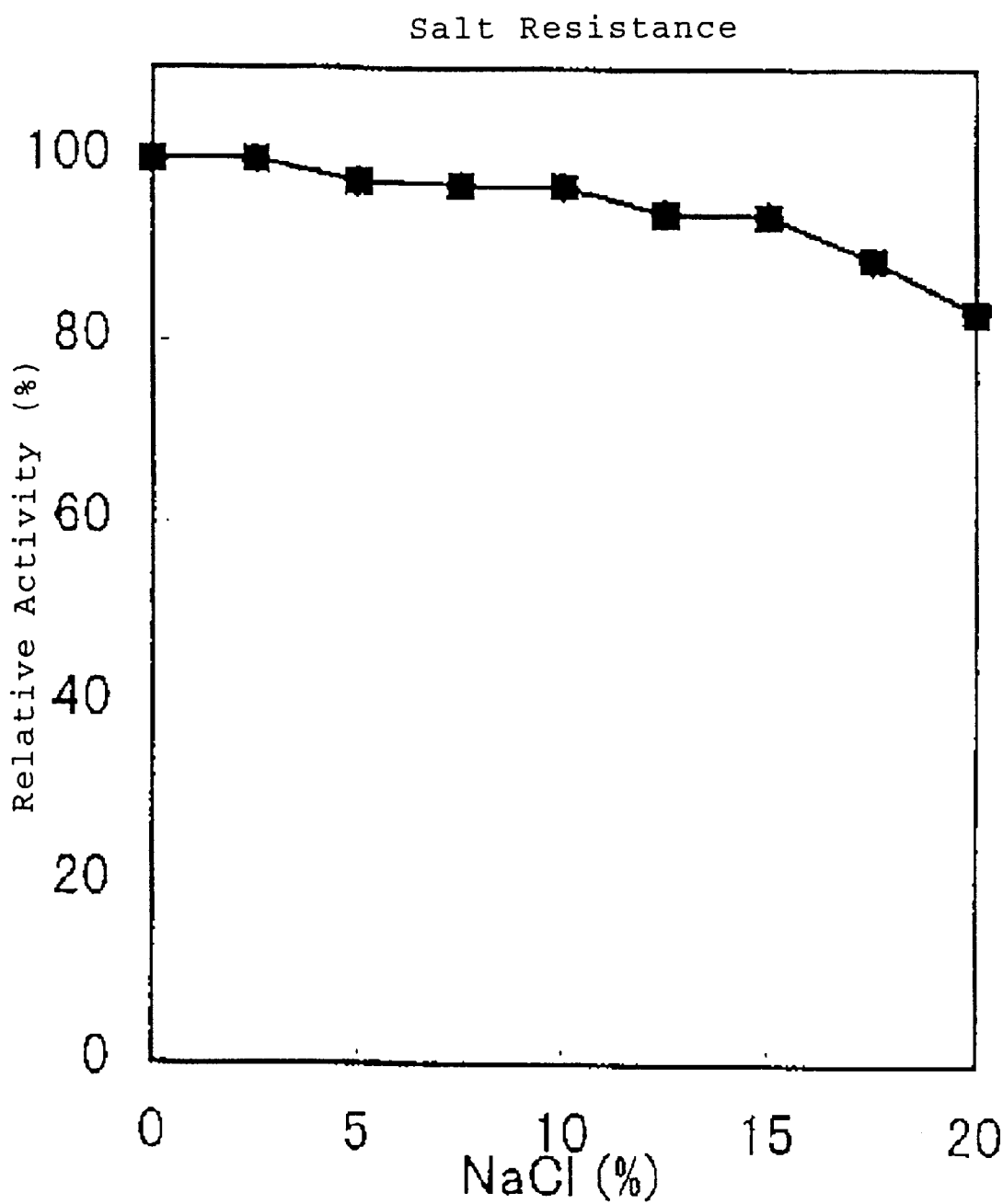
FIG. 1 shows the salt resistance of the salt-resistant thermostable glutaminase derived from *Cryptococcus nodaensis*.

Hereinafter, the present invention is described in detail.

The present invention provides *Cryptococcus nodaensis* G60 having the following microbial characteristics.
(a) Cultural and morphological characteristics
i) YM liquid medium
 cell size: 3 to 5×5 to 10 μm
 shape: lemon-shaped to spindle-shaped
 vegetative multiplication: multipolar budding
2) YM agar medium
 Slightly elevated in a lens form and smooth at the periphery. The surface is smooth and glossy. Cream color. Viscous.
3) Dalmau plate culture in corn meal agar medium
 Formation of pseudomycelia, oidiospores, chlamydospores, teliospores, basidiospores, and ballistospores are not observed.
(b) Formation of ascospores
 Formation of ascospores is not observed in any of YM agar medium, Gorodkowa, Fowell agar medium, malt agar medium, and V-8 agar medium.
(c) Physiological and chemical taxonomic characteristics
1) Conditions for Optimum growth
 Temperature 25° C.
 pH 5.7–6.5
2) Range of conditioned for growth
 Temperature 4–30° C.
 pH 2.7–10.0
3) Assimilation of nitrates
 Nitrates: assimilable
 Nitrites: assimilable
4) Degradation of fat
 Positive
5) Degradation of urea
 Positive
6) Diazonium blue B reaction
 Positive
7) Liquefaction of gelatin
 Positive
8) Resistance to salt (NaCl)
 5%
9) Formation of carotenoid
 Negative
10) Significant formation of organic acids
 Negative
11) Formation of starch-like substance
 Positive
12) Requirement for vitamin
 Not required.
13) Assimilability and fermentability of carbon sources

| Carbon Source | Assimilability | Fermentability |
|---|---|---|
| Lactose | + | − |
| N-Acetyl-D-glucosamine | − | |
| D-glucosamine | − | |
| Arbtin | − | |
| Galactose | + | − |
| Sorbose | − | |
| Sucrose | + | − |
| Maltose | + | − |
| Cellobiose | + | − |
| Trehalose | + | − |
| Melibiose | + | − |
| Raffinose | + | − |
| Melezitose | + | − |
| Starch | + | − |
| D-Xylose | + | − |
| L-Arabinose | D | − |
| D-Arabinose | + | − |
| D-Ribose | + | − |
| L-Rhamnose | + | − |
| Glycerol | D | − |
| Erythritol | D | − |
| Ribitol | + | − |
| Galactitol | + | − |
| D-Mannitol | + | − |
| D-glucitol | + | − |
| Salicin | + | − |
| DL-Lactic acid | D | − |
| Succinic acid | + | − |
| Citric acid | W | − |
| Inositol | + | − |
| Inulin | − | − |
| Methanol | − | − |
| Ethanol | D | − |
| D-Glucose | + | − |
| α-Methyl-Glucoside | + | − |
| D-gluconate | + | − |

(+, positive; −, negative; W, weak; D, delayed but positive)

14) Growth in YM liquid medium containing 50% D-glucose
 Weak
15) Growth in YM liquid medium containing 60% D-glucose
 No growth
16) Formation of extracellular DNase
 Positive
17) GC content and ubiquinone
 56.9 mol-% and Q-10
18) DNA-DNA homology with related species
 DNA-DNA homology analysis was examined by a coloration method using a microplate in accordance with the method of Ezaki et al. (J. Clin. Microbiol., 29, 1569–1603 (1991)).

The results are shown in Table 3.

From the microbial characteristics described above, the position of the above strain in microbial classification was determined on the basis of "The yeast, a taxonomic study".

The characteristics of *Cryptococcus nodaensis* G60 are: (1) production of extracellular DNase, (2) positive DBB reaction, (3) positive urease activity, (4) no formation of teliospores, ballistospores, and basidiospores, (5) no formation of pseudomycelia, (6) formation of starch-like substance, (7) assimilation of inositol, (8) assimilation of erythritol, and (9) its related species (for the reason of the absence of requirement for vitamin for growth) being *Cryptococcus laurentii* (abbreviated hereinafter to *C. lau*) and *Cryptococcus luteolus* (abbreviated hereinafter to *C. lut*).

However, as shown in Table 2, "G60" is different from with the related species *C. lau* and *C. lut* in respect of its microbial character, and, as shown in Table 3, "G60" is different from the related species in respect of DNA-DNA homology. That is, the comparison of "G60" with the two related species indicates DNA-DNA homology as low as about 10%. Accordingly, "G60" was identified as a new species of the genus Cryptococcus and designated *Cryptococcus nodaensis* G60 (hereinafter also called G60), and deposited as FERM BP-6351 on May 13, 1998 with the National Institute of Bioscience and Human-Technology, Agency of Industrial Science and Technology, Japan. This organism is irrevocably and without restriction or condition available to the public.

TABLE 2

Comparison in microbial characteristics among G60 and the related species

|  | G60 (present invention) | *C. lau* related species | *C. lut* |
|---|---|---|---|
| 1) Assimilability |  |  |  |
| Lactose | + | + | − |
| N-Acetyl-D-glucosamine | − | + | + |
| D-glucosamine | − | + | v |
| Arbtin | − | + | − |
| 2) Growth at 32° C. | − | + | + |
| 3) Degradation of fat | + | − | + |
| 4) Cycloheximide resistance |  |  |  |
| 100 ppm | + | − | w |
| 1000 ppm | w | − | w |
| 5) Salt resistance growth limit conc of NaCl (%) | 5 | 10 | 9 |

TABLE 3

Comparison of DNA-DNA homology among G60 and the related species

|  | G60 (present invention) | *C. lau* related species | *C. lut* |
|---|---|---|---|
| G60 (present invention) | 100 | 7 | 8 |
| *C. lau* (related species) | 11 | 100 | 12 |
| *C. lut* (related species) | 8 | 9 | 100 |

Hereinafter, the physicochemical characteristics (salt resistance, thermostability, optimum pH, optimum temperature etc.) of the glutaminase derived from *Cryptococcus nodaensis* G60 are described.

Preparation of an enzyme solution

The cells itself of *Cryptococcus nodaensis* G60 (or its treated material) is suspended in water or a buffer to prepare a glutaminase enzyme solution.

That is, *Cryptococcus nodaensis* G60 was inoculated into a medium (pH 5.5) consisting of 3.0% glucose, 0.5% yeast extract, 0.1% $KH_2PO_4$ and 0.1% $MgSO_4$ and then cultured at 25° C. for 4 days under shaking.

The cells (or its treated material) was separated from the culture and added to water or a buffer to prepare the enzyme solution.

(a) A method of measuring the glutaminase activity

A method of quantifying L-glutamic acid formed by hydrolysis of L-glutamine.

2.0 ml of 0.2 M acetate buffer and 1.0 ml of the present enzyme solution were added to 1.0 ml of 2% (w/v) L-glutamine solution, and the mixture was reacted at 37° C. for 30 minutes, and then the reaction was terminated by adding 1.0 ml of 0.75 N perchloric acid, and 0.5 ml of 1.5 N sodium hydroxide was added thereto to neutralize the reaction solution.

Then, 1.0 ml of 0.1 M hydrochloric acid-hydroxylamine buffer (pH 8.0) containing 50 mM EDTA·Na, 1.0 ml of 20 mM $NAD^+$ solution, and 50 μl of 500 U/ml L-glutamate dehydrogenase were added to 0.1 ml of the above reaction solution, and the mixture was reacted at 37° C. for 30 minutes and the absorbance at 340 nm was measured with a spectrophotometer.

Then, the amount of L-glutamic acid formed was determined using a previously prepared calibration curve of L-glutamic acid, and the glutaminase activity was determined assuming that the amount of the enzyme forming 1 μM glutamic acid per minute at 37° C. is 1 U.

(b) Salt resistance:

Salt was added to the glutaminase reaction system and the glutaminase activity was measured.

The results are shown in FIG. 1.

As can be seen from the results in FIG. 1, the enzyme of the present invention in the presence of 18% (w/v) salt exhibits at least 85% enzyme activity relative to 100% activity in the absence of salt.

(c) Thermostability:

The enzyme solution was treated at predetermined temperatures for 10 to 30 minutes and then measured for its activity.

Figure 2:
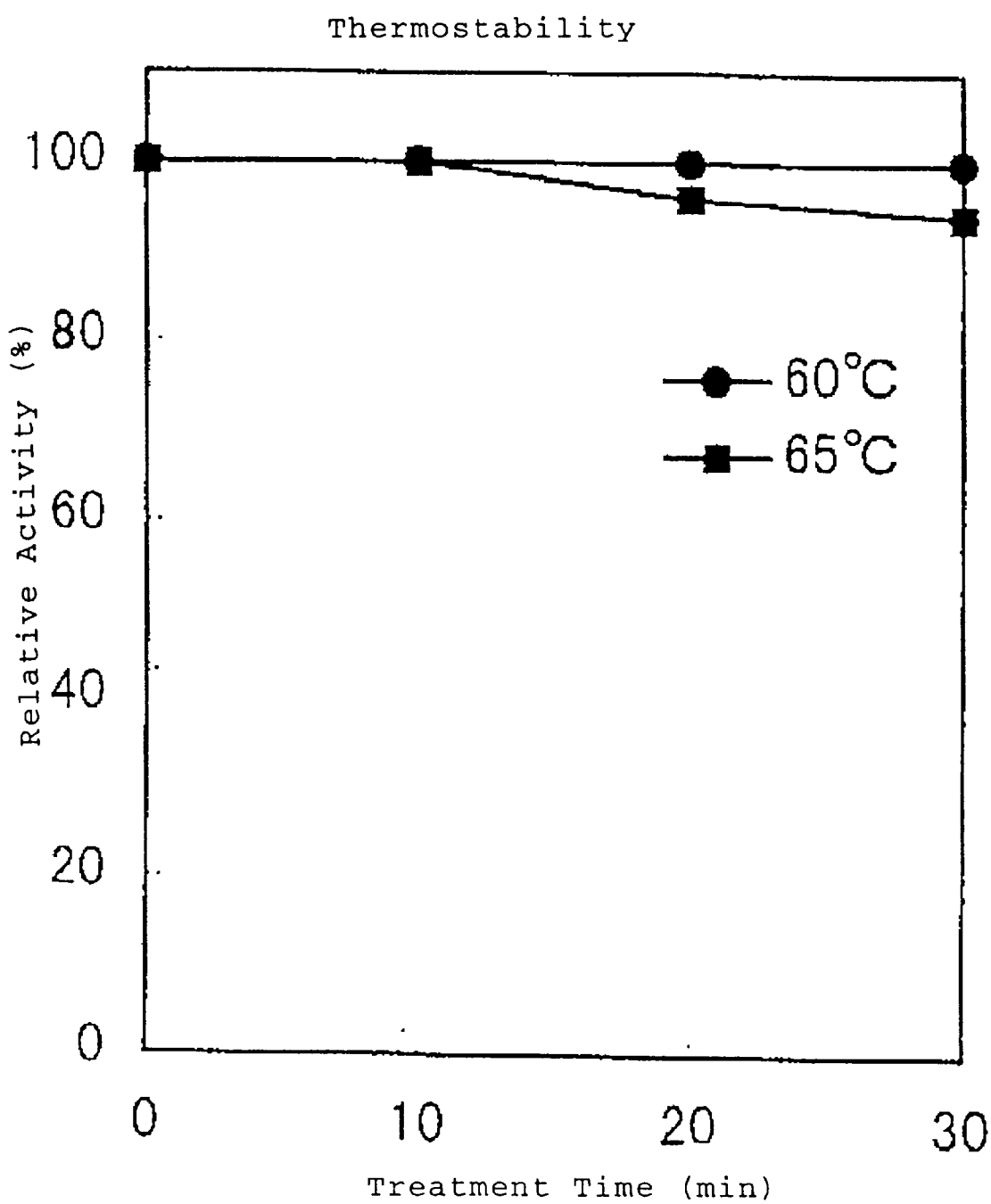
FIG. 2 shows the thermostability of said enzyme.

The results are shown in FIG. 2.

As can be seen from the results in FIG. 2, the enzyme of the present invention does not decrease its activity even after treatment at 60° C. for 30 minutes and maintains 90% or more enzyme activity even after treatment at 65° C. for 30 minutes, relative to 100% activity measured at 25° C., so the enzyme exhibits very high thermostability.

Although not shown the enzyme of the present invention exhibits 70% relative activity after treatment at 70° C. for 10 minutes, indicating that the enzyme has about twice as high thermostability as that of the known salt-resistant thermostable glutaminase (relative activity: 34%) derived from *Candida famata* KM-1.

(d) Optimum pH

The glutaminase reaction system was adjusted to pH 3.0–6.0 (acetate buffer) and pH 6.5–8.0 (phosphate buffer) to measure the activity.

Figure 3:
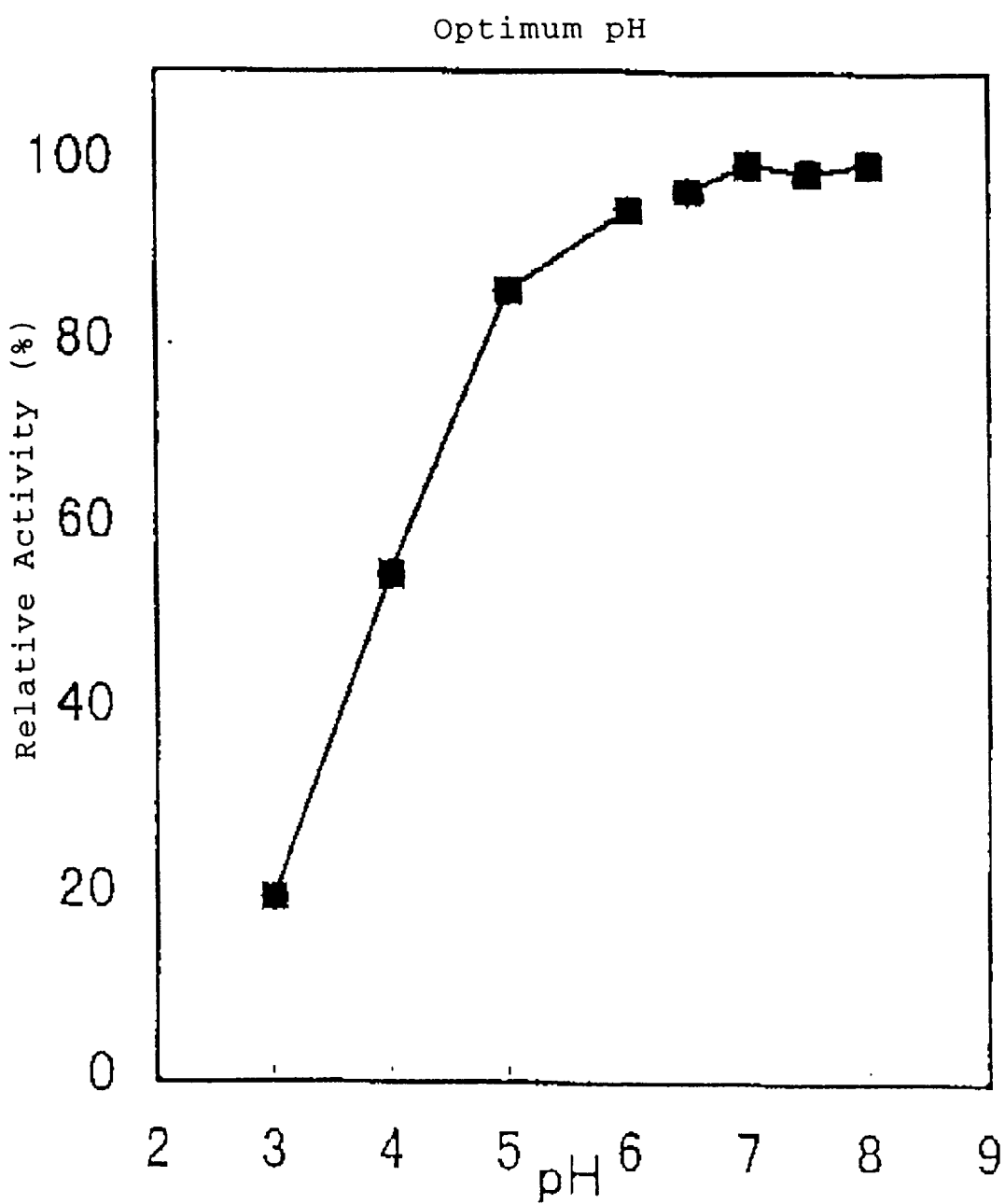
FIG. 3 shows the optimum pH of said enzyme.

The results are shown in FIG. 3.

As can be seen from the results in FIG. 3, the optimum pH of the present enzyme is 5.0 or more, particularly 5.0 to 8.0.

(e) Optimum temperature

The temperature in the glutaminase reaction system was varied between 30 to 80° C. to measure the activity.

Figure 4:
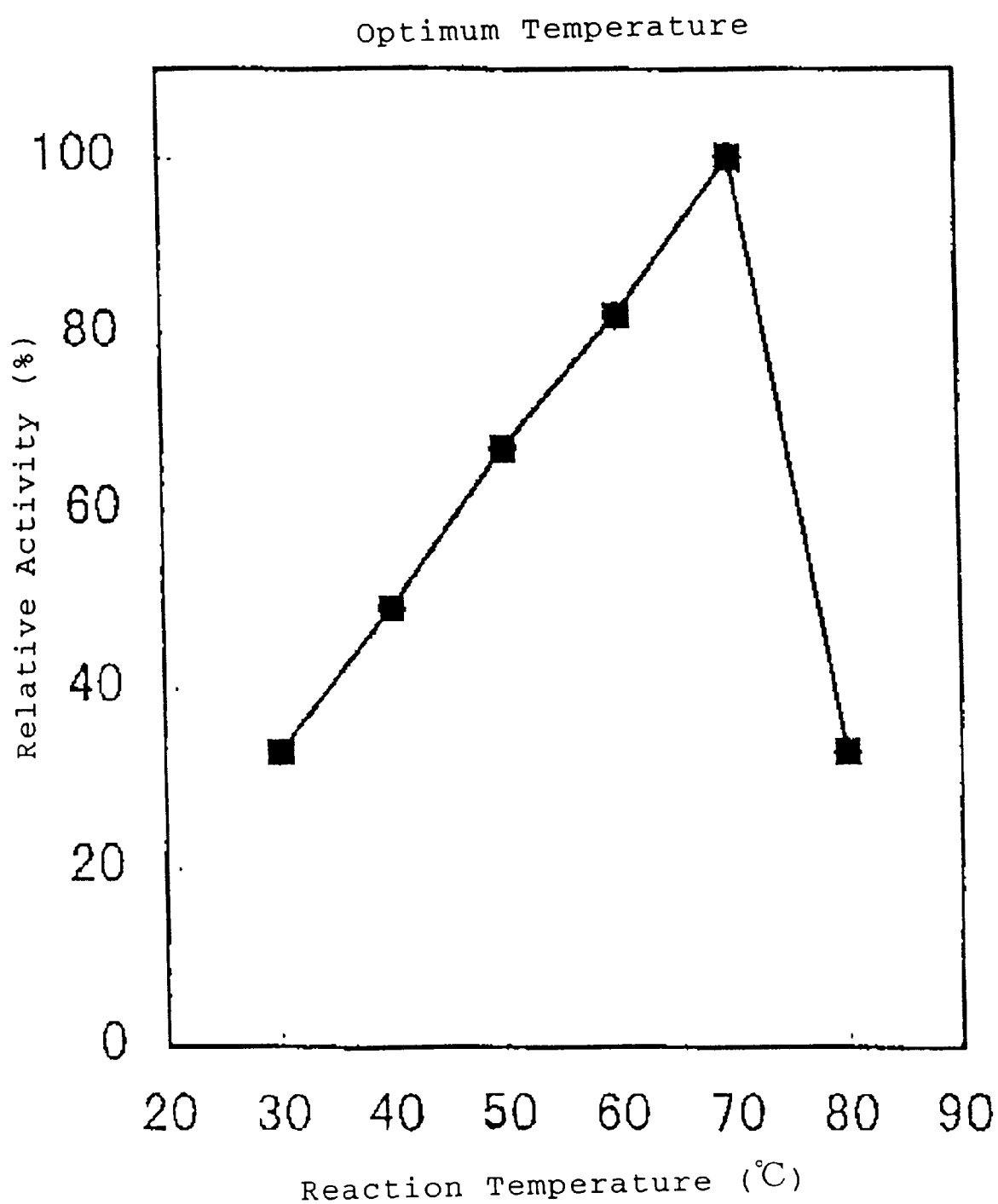
FIG. 4 shows the optimum temperature of said enzyme.

The results are shown in FIG. 4.

As can be seen from FIG. 4, the optimum temperature of the present enzyme is 70° C.

Although not shown the present enzyme has 70% or more relative activity even at a low pH value of 3.5.

Now, a description is made of a process for producing the salt-resistant thermostable glutaminase, which comprises culturing a microorganism belonging to a new species *Cryptococcus nodaensis* having the ability to produce the salt-resistant thermostable glutaminase thereby producing the salt-resistant thermostable glutaminase, and then recovering it.

Usually, the culture method is advantageously a method of using a liquid culture under aeration, for example, shake culture in a flask or culture under aeration in e.g. a jar or tank fermenter equipped with a stirring device for aeration.

The culture temperature ranges preferably from 25 to 28° C., and the culture time is preferably 16 hours or more.

The medium used is preferably a liquid medium, and nutrient sources added to the medium are various nutrient sources generally used for culturing microorganisms.

That is, carbon sources include e.g. monosaccharides and oligosaccharides such as glucose, maltose etc. and other carbon sources such as glycerin etc., and nitrogen sources include e.g. peptone, meat extract, yeast extract, corn steep liquor, casamino acid, nonfat soy bean extract, wheat gluten hydrolysates, ammonium salts, nitrates etc. Further, salts with magnesium, calcium and sodium, phosphates, and trace nutrient elements may be added.

The culture liquid thus obtained may be subjected to solid/liquid separation (e.g. filtration, centrifugation etc.), and the cells is separated to give the salt-resistant thermostable glutaminase of the present invention. The cells thus obtained has the character that the cells itself or even after killed by heating can be used sufficiently as a glutaminase source. The treated material of the cells includes a material obtained by partially disrupting the cells by grinding, a crude enzyme obtained by allowing a lytic enzyme to act on the cells to release and collect the present enzyme from the cells, and a purified enzyme obtained by purifying said crude enzyme.

To release the enzyme from the cells, conventional enzyme extraction methods can be applied. For example, it is possible to use mechanical grinding and disruption; sonication or ultrasonication; disruption with a high-pressure homogenizer; lysis of the cells by lysozyme-containing materials such as a culture liquid derived from the genus Trichoderma having the ability to produce a lysozyme, or by a lytic enzyme obtained from said culture liquid; autolysis; and osmotic shock procedure. By these techniques, a crude enzyme solution of the salt-resistant thermostable glutaminase can be prepared.

The resulting crude enzyme solution is lyophilized as such in vacuo or it is further fractionated with ammonium sulfate, alcohol or acetone to give glutaminase active fractions which are collected, dialyzed against pure water and lyophilized in vacuo, whereby a crude enzyme preparation of the salt-resistant thermostable glutaminase can be obtained.

To obtain the purified enzyme from the crude enzyme solution, the above crude enzyme preparation may be subjected to a suitable combination of adsorption-elution using various kinds of ion exchangers, for example DEAE-cellulose, TEAE-cellulose, QAE-Sephadex and hydroxyapatite gel filtration using Sephadex G-150, G-200 etc. adsorption-elution using Celite, and electrophoresis on polyacrylamide gel whereby a highly purified enzyme preparation can be obtained.

Further, the present invention provides a process for producing glutamic acid-rich protein hydrolysates which comprises adding the new species *Cryptococcus nodaensis* or its treated material at the time of hydrolysis.

Specifically, the new species *Cryptococcus nodaensis* or its treated material can be added in the step of mixing or the step of fermentation and aging in a process for producing soy sauce by fermentation in which thermally denatured proteinous materials (e.g. soybeans, nonfat soybeans, gluten etc.) are mixed with thermally denatured starchy materials (rice, wheat, corn etc.), and after the water content of the mixture is adjusted to 30–45%, koji is inoculated into it and cultured in a usual manner to give solid koji (soy sauce koji) which is then mixed with saline and subjected to fermentation and aging.

Further, the new species *Cryptococcus nodaensis* or its treated material can be added in the step of mixing in a process for producing miso by fermentation in which koji is inoculated into starchy materials (rice, wheat, corn etc.) containing suitable volume of water and cultured in a usual manner to give solid koji, and thermally denatured proteinous materials (soybeans, broad beans, peas etc.) and salt are added to and mixed uniformly with the solid koji, followed by fermentation and aging.

Further, the new species *Cryptococcus nodaensis* or its treated material can be added in a process for producing food and drink containing peptides and/or amino acids as a part or a majority of tasting components, in which protein materials or protein-containing materials are hydrolyzed with a proteolytic enzyme or a proteolytic enzyme-containing material (including solid koji) in the presence or absence of salt at room temperature to 80° C.

The activity of the salt-resistant thermostable glutaminase according to the present invention is hardly inhibited by high temperatures and salt even in the presence of high conc. salt at high temperatures. Accordingly, when the present enzyme is used for protein hydrolysis at high temperatures and in the presence of high conc. salt in producing glutamic acid-rich seasoning foods etc., then foods significantly reinforced with glutamic acid as a tasting component can be obtained efficiently, so the present invention is extremely useful in food industry.

EXAMPLES

EXAMPLE 1

Preparation of Salt-Resistant Thermostable Glutaminase

*Cryptococcus nodaensis* G60 was inoculated into a medium pH 5.5, consisting of 3.0% glucose, 0.5% yeast extract, 0.1% $KH_2PO_4$, and 0.1% $MgSO_4$, and then cultured at 25° C. for 4 days under shaking to give a seed culture.

This seed culture was inoculated into 15 L medium with the same composition as above, and cultured in a 30-L jar fermenter at an aeration rate of 20 L/min., at a stirring rate of 300 rpm at 25° C. for 30 hours to give a culture containing the grown cells.

This culture was concentrated 10-fold by centrifugation and heated at 50° C. for 30 minutes to kill the cells whereby a crude enzyme preparation usable as a source of the salt-resistant thermostable glutaminase was prepared.

EXAMPLE 2

Preparation of a Purified Enzyme Preparation

The culture containing the grown cells in Example 1 was centrifuged, and a part (200 g) of the microbial paste thus obtained was collected, added to 2.0 L of 0.2 M acetate buffer (pH 5.0) and suspended well therein, and 16 g of Cellulase Onozuka R-10 (Yakult Honsha Co., Ltd.) was added as lysozyme to it, and the mixture was stirred at 42° C. for 12 hours, followed by centrifugation (8000 rpm, 20 minutes) to give a supernatant.

This supernatant was heated at 60° C. for 1 hour, then adjusted to pH 7.0 with 0.2 M $K_2HPO_4$, and further heated at 60° C. for 1 hour to denature contaminant proteins, and the proteins thus denatured were removed by centrifugation (8000 rpm, 20 minutes).

To the supernatant thus obtained was added 2-fold volume of acetone (−20° C.), and the mixture was well stirred, then kept at 4° C. for 5 hours and centrifuged (8000 rpm, 20 minutes) to collect the precipitates.

The precipitates were dissolved in 0.02 M acetate buffer (pH 6.0) and dialyzed against 0.02 M acetate buffer (pH 6.0).

The resulting crude enzyme solution was applied to a DEAE-Sepharose CL-6B column (Pharmacia) previously equilibrated with 0.02 M acetate buffer (pH 6.0). The enzyme thus adsorbed thereon was washed sufficiently with 0.02 M acetate buffer (pH 6.0) and eluted with a gradient of 0 to 0.5 M NaCl, and the active fractions were collected.

Then, this enzyme solution was dialyzed against 0.1 M acetate buffer containing 0.5 M ammonium sulfate and 20% (w/v) ethylene glycol, and then adsorbed onto a Phenyl-Sepharose column (Pharmacia) previously equilibrated with the same buffer as above, and the protein was washed with the same buffer and eluted with a gradient of both 0.5 to 0 M sulfate ammonium and 20 to 60% ethylene glycol respectively, and the active fractions were collected. The resulting enzyme solution was concentrated using an ultrafiltration unit (fractional molecular weight of 10000, Amicon) and dialyzed against 0.02 M phosphate buffer (pH 6.0).

This enzyme solution was adsorbed onto a hydroxyapatite column (Nakarai) previously equilibrated with 0.02 M phosphate buffer (pH 6.0), washed with the same phosphate buffer, and eluted with a gradient of 0.02 to 0.3 M phosphate, and the active fractions were collected.

The resulting enzyme solution was concentrated using the same ultrafiltration unit as mentioned above.

The enzyme solution thus concentrated was applied to a Sephacryl S-300 column (1.2×100 cm) previously equilibrated with 0.1 M phosphate buffer (pH 6.0) containing 0.2 M salt and then subjected to gel filtration.

The resulting active fractions were combined and concentrated with Centricon (fractional molecular weight of 30,000, Pharmacia), and the resulting enzyme solution was separated by HPLC on TSK gel G3000 SW (Tosoh Corporation) to give 13.3 mg homogeneous enzyme preparation.

The specific activity of this enzyme was 65 U/mg.

EXAMPLE 3

Production of Glutamic Acid-Rich Soy Sauce

Koji was inoculated into a mixture of 5 kg of nonfat soybeans and 5 kg wheat, and soy sauce koji was obtained therefrom according to a conventional process for producing soy sauce koji. This soy sauce koji was introduced into 17.5 L of 25% saline, and the thermally treated material of *Cryptococcus nodaensis,* prepared in Example 1, was added thereto as a glutaminase source, and the mixture was subjected to fermentation control for flavorings in a usual manner, and 6 months thereafter, aged flavorings were obtained, and these are filtered under pressure to give soy sauce.

For comparison, control soy sauce was obtained in the same manner as in the above process for producing soy sauce except that "*Cryptococcus nodaensis*" was not added.

Also for comparison, comparative soy sauce was obtained in the same manner as described above except that "*Cryptococcus albidus* ATCC-20293" (abbreviated hereinafter to *C. alb*) was used in place of *Cryptococcus nodaensis*".

The three kinds of soy sauce thus obtained were examined for total nitrogen (abbreviated to TN), glutamic acid (abbreviated to Glu), and Glu/TN, respectively.

The results are shown in Table 4.

TABLE 4

| Strains used | Glutaminase added (Unit) | TN | Glu/TN |
|---|---|---|---|
| No addition (control) | — | 1.763 | 0.62 |
| C. alb (comparative example) | 200000 | 1.813 | 0.73 |
| G60 (present invention) | 5000 | 1.815 | 0.72 |
|  | 10000 | 1.821 | 0.77 |
|  | 20000 | 1.822 | 0.79 |
|  | 30000 | 1.825 | 0.80 |

As can be seen from the results in Table 4, glutamic acid-rich and highly flavoring soy sauce with high water-soluble nitrogen (total nitrogen) levels can be obtained efficiently by adding *Cryptococcus nodaensis* G60 in a very smaller amount (i.e. 1/40) as compared with *C. alb.*

EXAMPLE 4

Production of Glutamic Acid-Rich Protein Hydrolysate Liquid

About 5 g of a commercial protease preparation "Sumizyme MP" (Shin Nippon Kagaku Kogyo K. K.), 117 g of salt, and 980 ml water were added to 350 g of gluten, and 10,000 U each of *C. alb* and G60 were added as a glutaminase source, and the mixture was subjected to enzyme digestion at 40° C. for 48 hours to give a protein hydrolysate with about 10% salt. After finished, the reaction solution was squeezed and measured for Glu/TN.

As a control, a reaction solution was obtained in the same manner as above except that the glutaminase source was not added, and measured in the same manner.

TABLE 5

| Strains used | Glutaminase added (Unit) | TN | Glu | Glu/TN |
|---|---|---|---|---|
| No addition | — | 2.451 | 0.907 | 0.37 |
| C. alb | 10000 | 2.556 | 3.527 | 1.38 |
| G60 | 10000 | 2.572 | 4.038 | 1.57 |

(Note)
TN = total nitrogen (Unit: % (w/v))
Glu = glutamic acid (Unit: %/ml)

As can be seen from the results in Table 5, Glu was 3.527 in the case of *C. alb,* whereas in the case of *Cryptococcus nodaensis* G60 of the present invention, Glu was about 14% higher (i.e. 4.038) and the ratio of glutamic acid to water-soluble total nitrogen (Glu/TN) is high, so a protein hydrolysate liquid also excellent in tasting can be obtained.

All publications and patent documents cited herein are incorporated by reference in their entirety.

We claim:

1. An isolated Cryptococcus species, wherein said Cryptococcus species is *Cryptococcus nodaensis,* and wherein said *Cryptococcus nodaensis* is capable of assimilating lactose but is incapable of assimilating N-acetyl-D-glucosamine, D-glucosamine, and arbtin.

2. The *Cryptococcus nodaensis* of claim 1, wherein said species is *Cryptococcus nodaensis* G60.

3. A method for the production of salt-resistant thermostable glutaminase, comprising the steps of culturing *Cryptococcus nodaensis* under conditions such that said salt-resistant glutaminase is produced, isolating said salt-resistant glutamine from said *Cryptococcus nodaensis,* and recovering said salt-resistant glutaminase.

4. The method of claim 3, wherein said *Cryptococcus nodaensis* is *Cryptococcus nodaensis* G60.

5. A method for the production of glutamic acid-rich protein hydrolysates, comprising the steps of providing a protein source and thermostable glutaminase isolated from *Cryptococcus nodaensis* under conditions such that said protein source is hydrolyzed to produce said glutamic acid-rich protein hydrolysate.

6. The method of claim 5, wherein said protein hydrolysates comprise soy sauce.

7. A method for the production of glutamic acid-rich protein hydrolysates, comprising the steps of providing a protein source and *Cryptococcus nodaensis* under conditions such that said protein source is hydrolyzed to produce said glutamic acid-rich protein hydrolysate.

8. The method of claim 7, wherein said protein hydrolysates comprise soy sauce.

* * * * *

UNITED STATES PATENT AND TRADEMARK OFFICE
CERTIFICATE OF CORRECTION

PATENT NO. : 6,063,409
DATED      : 05/16/2000
INVENTOR(S): Itsuo Sato et al.

It is certified that error appears in the above-identified patent and that said Letters Patent is hereby corrected as shown below:

At column 11, line 13, please delete "glutamine" and insert -- glutaminase --.

Signed and Sealed this

Tenth Day of April, 2001

Attest:

NICHOLAS P. GODICI

*Attesting Officer*    *Acting Director of the United States Patent and Trademark Office*